United States Patent [19]

Layer et al.

[11] Patent Number: 4,629,752
[45] Date of Patent: Dec. 16, 1986

[54] SUBSTITUTED OXO-PIPERAZINYL-TRIAZINES AND UV LIGHT STABILIZED COMPOSITIONS

[75] Inventors: Robert W. Layer, Cuyahoga Falls; John T. Lai, Broadview Heights; Pyong N. Son, Akron, all of Ohio

[73] Assignee: The B. F. Goodrich Company, Akron, Ohio

[21] Appl. No.: 757,717

[22] Filed: Jul. 22, 1985

[51] Int. Cl.$^4$ .................. C08K 5/34; C07D 251/70; C07D 251/52; C07D 401/14
[52] U.S. Cl. ................................ 524/100; 524/96; 544/113; 544/198; 544/209
[58] Field of Search .............. 544/113, 198, 209; 524/96, 100

[56] References Cited

U.S. PATENT DOCUMENTS 4,480,092 10/1984 Lai et al. .................. 544/209
4,547,538 10/1985 Lai et al. .................. 524/100

Primary Examiner—John Kight
Assistant Examiner—Kriellion Morgan
Attorney, Agent, or Firm—A. D. Lobo; A. A. Csontos

[57] ABSTRACT

A particular branched chain polyalkylenepolyamine ("PAPA") having plural amine groups including a secondary amine group intermediate terminal free primary amine groups (that is, neither one is hindered), and having at least two C atoms between each group, may be selectively cyclized with a ketoform reaction to form a polysubstituted piperazinone ("PSP"), with specific directivity. Such PSPs are linked to a triazine nucleus to yield piperazinone-triazine ("PIP-T") compounds which are excellent stabilizers for polyolefins and other light-degradable polymers. Certain acyclic polyalkylenepolyamines may have a PIP-T substituent at each N atom forming pendant PIP-Ts ("P[PIP-T]" for brevity) which are also excellent stabilizers, and like some of the PIP-Ts, some P[PIP-T]s provide photostabilization without noticeably interfering with the color of films and fibers provided by even pastel-colored pigments and dyes.

20 Claims, No Drawings

SUBSTITUTED OXO-PIPERAZINYL-TRIAZINES AND UV LIGHT STABILIZED COMPOSITIONS

BACKGROUND OF THE INVENTION

This invention is related to 2-oxo-piperazinyl-triazine ("PIP-T" for brevity) compounds in which a polysubstituted piperazinone ("PSP") substituent is linked to the triazine ring through a single N (nitrogen) atom and at least two C (carbon) atoms, hence termed "distally linked". The term "polysubstituted" refers specifically to a piperazinone ring in which at least the $N^4$-adjacent C atoms (at the 3 and 5 positions) are each dialkyl-substituted, or one of the 3 or 5 C atoms is shared by a spiro cycloalkylene substituent, and the other is dialkyl-substituted.

More particularly, this invention is related to PIP-T compounds in which the PSP is connected to the triazine ring with a branched bridge, so termed because the bridge includes at least three serially linked atoms, the first, a N atom bound to the triazine ring, then two C atoms, and the N-adjacent C atom is always disubstituted.

PIP-T compounds including bis compounds and oligomers thereof having a polymethylene bridge (unbranched) are disclosed in our U.S. Pat. No. 4,480,092 ("the '092 patent") for use as ultraviolet ("UV") light stabilizers in organic materials, whether natural or synthetic, which are to be protected against degradation by UV light by incorporating a UV light stabilizer in the material.

Many classes of compounds are known to be useful UV light stabilizers, some being more effective than others. Particularly effective 2-keto-diazacycloalkanes which provide stabilized compositions resistant to degradation by UV light, include the 2-keto-1,4-diazacycloalkanes disclosed in U.S. Pat. No. 4,190,571; and, the 2-keto-1,5-diazacycloalkanes disclosed in U.S. Pat. No. 4,207,228. Other 2-keto-diazacycloalkanes useful as UV light stabilizers are disclosed in U.S. Pat. Nos. 3,919,234; 3,920,659; and 3,928,330 which teach substituted piperazinediones. Cycloalkanes useful as UV light stabilizers are disclosed in Ger. Offen. No. 2,315,042; Japanese Pat. Nos. 7,453,571 and 7,453,572.

The compounds of this invention belong to a well-recognized chemical class of UV light stabilizers known as multi-ringed triazine derivatives. Though most such derivatives disclosed as UV light stabilizers have a significant level of UV-stabilization ("UV-S") activity, each has one or more serious drawbacks which makes the one less desirable from a practical, utilitarian point of view, than another having a less serious drawback. This reality dictates the unending search, even in the narrow field of multi-ringed triazine derivatives, for compounds with better UV-S activity, and results in discarding numerous multi-ringed triazine derivatives which have no appreciable UV-S activity, if at all.

Prior art multi-ringed triazine derivatives with UV-S activity are also disclosed in U.S. Pat. Nos. 4,086,204; 4,051,137; 4,108,829; French Pat. No. 2181 059; and, Japanese Pat. No. 51-4247; inter alia.

In particular regard to our '092 patent, we found that a distally linked PSP was unexpectedly effective not only for its UV-S activity, but also for its antioxidant ("AO") activity, particularly in combination with certain hindered phenols, as disclosed in our copending patent application Ser. No. 721,270 filed Apr. 9, 1985.

We disclosed in our '092 patent how to provide a bridge of plural atoms for the critical distally linked rings. We started with a particular class of alkylated polyalkylenepolyamine ("PAPA"), namely a N-(alkyl)-N'-(aminoalkyl/aryl/aralkyl/cycloalkyl)-1,p-alkanediamine, wherein "p" is the number of methylene C atoms (hereafter "2AAD" for brevity), and one primary amine group was free, the other was substituted and hindered. The process comprises reductively alkylating a particular class of PAPA, such as a N'-(aminoalkyl/aryl/aralkyl/cycloalkyl)-1,p-alkanediamine (hereafter "2AD" for brevity) with a ketone in the presence of a Group VIII metal hydrogenation catalyst and a solvent for the reactants, by carrying out the reaction under elevated temperature and pressure to produce the 2AAD compound; separating the solvent from the reaction mass; adding chloroform and a ketone, preferably in the presence of a phase transfer catalyst; and, carrying out the reaction to produce a PSP which is recovered. The PSP is then reacted with cyanuric chloride or other reactive triazine compound. In a particular preferred embodiment of the invention, a PSP is produced from 2AD using a ketone as a reactant to produce 2AAD; and then, again using a ketone as a reactant, to cyclize the 2AAD. The PSP is then coupled with a triazine ring-containing compound to provide at least one distally linked PSP substituent on the triazine ring.

The phase transfer catalyzed reaction referred to hereinabove is known as the "ketoform reaction" disclosed in greater detail in U.S. Pat. No. 4,167,512, also in an article titled "Hindered Amines. Novel Synthesis of 1,3,3,5,5-Pentasubstituted 2-Piperazinones" by John T. Lai in *J. Org. Chem.* 45, 754 (1980), and in our '092 patent, relevant parts of all of which are incorporated by reference thereto as if fully set forth herein.

The ketoform reaction may also be carried out without a phase transfer catalyst as disclosed in U.S. Pat. No. 4,466,915 which is incorporated by reference thereto as if fully set forth herein.

The "2AAD" compound, for example, N-(2-butyl)-N'-(2-amino-2-methylpropyl)-1,2-ethanediamine (identified as 1A herebelow), provided a hindered primary amine group by introducing a substituent at the N-position, which is precisely where it was needed to allow us to use the subsequent ketoform reaction to close the ring and form the PSP by connecting the unhindered primary amine group and the intermediate secondary amine group. It was this blocking of the N-position which so effectively allowed cyclization of the unhindered primary amine group and the next adjacent secondary amine group with such regioselective specificity, as was noted in the Lai article, supra.

Thus, it became evident, and it was our belief at that time, that the desired reaction required that one unhindered primary amine group only be left on a 2AAD if it was to be cyclized effectively. It was obvious that if two unhindered primary amine groups were present on a 2AAD, each would be equivalent to, and as active as, the other, and, in a ketoform reaction, both would react with the chloroform generating a trichloromethide ion, in turn resulting in an array of unwanted compounds, few, if any, of which would be cyclized so as to have formed the piperazinone ring.

This invention documents the error of that belief. We accidentally found that the desired reaction proceeded with unhindered or "free" terminal primary amine groups. In other words, blocking the N-position, by converting the primary amine group to a secondary amine group, could be avoided if we disubstituted the C atom adjacent the N-position, thus making both terminal primary amine groups equivalent and equally unhindered. After the ketoform reaction, after the PSP is formed, we are left with a terminal free primary amine group—a fortuitous discovery which leaves the free primary amine to react directly with a reactive triazine compound. From an economic point of view, this is highly fortunate.

Typically, PIP-T compounds are used as photostabilizers ("PS") in conjunction with a hindered phenol antioxidant ("AO") This appears to be a peculiarity of PIP-T compounds since it has been found that there is generally a strong antagonistic effect between many a hindered amine light stabilizer ("HALS") and a hindered phenol AO used in combination for the stabilization of polymers (see "Photostabilizing Performance of a Hindered Piperidine Compound in Polypropylene Film: Antioxidant/Light Stabilizer Effects" by N. S. Allen *Polym. Degrad. Stabil.* 2, 129 (1980) and "Catalytic Thermal Oxidation of Phenolic Antioxidants by Hindered Piperidine Compounds" by N. S. Allen *Polym. Degrad. Stabil.*, 3, 73 (1980–81).

It was also known that a particular hindered phenol AO, namely tris(3,5-di-t-butyl-4-hydroxybenzyl-)isocyanurate* commercially available as Good-rite ®3114, and a bis(hindered piperidine) PS commercially available as Tinuvin ®770, showed an unexpectedly beneficial coaction, as disclosed in "Interaction Between Antioxidants and Hindered Piperidine Compounds in the Photostabilization of Polypropylene: Influence of Processing History" by N. S. Allen et al, *Polym. Photochem.* 1, 11 (1981).
*also named 1,3,5-tris[3,5-di-t-butyl-4-hydroxyphenyl)-methyl]-1,3,5-triazine-2,4,6-(1H,3H,5H)-trione It was further known that bis-1-(piperazin-2-one) provided not only excellent photostabilization properties as disclosed in U.S. Pat. No. 4,190,571 but also excellent AO properties, as disclosed in U.S. Pat. No. 4,309,336. Moreover, the bis-1-(piperazin-2-one), like many other hindered piperazin-2-one PS compounds, in combination with hindered phenol AOs, were more effective as both PSs and AOs than the sum of their individual effectiveness as PSs and AOs, as disclosed in "Hindered Diazacycloalkanones as UV Stabilizers and Antioxidants" by J. T. Lai et al *Polym. Preprints*, 25(1), 1984.

Yet, quite surprising is the disclosure that commercially available Chimassorb 944 when used in combination with BHT, Good-rite 3114 and Irganox 1010 is indeed less effective as determined by Weather-O-Meter tests (see brochure entitled "Light Stabilization of Polypropylene Multifilaments and Monofilaments" published by Chimosa S.P.A. (1978), FIG. 3.

From the foregoing unpredictable behavior of particular HALS in combination with hindered phenol AOs generally, it is evident that the effectiveness of any HALS which is structurally dissimilar from the foregoing HALS, ca be no more predictable. Certainly, there was no reason to expect that a compound from the particular class of HALS containing linked piperazinone and triazine rings, when combined with one of specific hindered phenols, would exhibit a higher degree of PS and AO activity than that obtained by summing the activity of the individual HALS and hindered phenol when used separately. This unique synergistic behavior of a PIP-T compound is now attributable to its being less basic, because of the 2-one group, than compounds containing linked triazine and pyridine, piperidine, or piperazine rings.

SUMMARY OF THE INVENTION

It has been discovered that a particular branched chain polyalkylenepolyamine ("PAPA") having plural amine groups including a secondary amine group intermediate terminal free primary amine groups (that is, neither one is hindered), and having at least two C atoms between each group (referred to herein as a "TFPA" compound because it has "terminal free primary amine" groups), may be selectively cyclized with a ketoform reaction to form a PSP, with quite unexpected specific directivity, in the same manner as with the ketoform reaction disclosed in our '092 patent.

It is therefore a general object of this invention to provide a process for cyclizing a TFPA compound comprising contacting the TFPA compound with a saturated cyclic or acyclic monoketone and a haloform, in the presence of (i) an organic solvent, (ii) solid or aqueous alkali, and optionally, (iii) a phase transfer catalyst. The phase transfer catalyst, if used, is selected from the group consisting of a tertiary or quaternary compound of an element selected from Groups VA and VIA of the Periodic Table, and a polyether.

It has further been discovered that when a PSP is distally linked to a triazine ring through at least a three-atom chain of serially linked 1 (one) N and 2 (two) C atoms, and the N-adjacent C atom in the chain is disubstituted, the novel compounds so formed are found to be exceptionally well-suited for use as stabilizers in synthetic resinous materials subject to degradation by uv light.

It is therefore a general object of this invention to provide a novel class of hindered amine-triazine derivatives useful as uv light stabilizers for polyolefins and other light-degradable polymers, which derivatives are characterized by (a) having at least one PSP distally linked to a triazine ring through a chain of serially linked N (adjacent the triazine ring) and at least two C atoms, the N-adjacent one of which is disubstituted, and (b) improved resistance to extraction from such polymers in prolonged contact with an aqueous solution.

It is another general object of this invention to provide a combination stabilizer for PS and AO stabilization of polymers, particularly polyolefins, in which combination an effective amount of each of two compounds is used, one from the class of PS compounds containing linked triazine and piperazinone rings, and the other a hindered phenol selected from the group consisting of tris(3,-5-di-t-butyl-4-hydroxybenzyl-)isocyanurate; 2,6-ditertiarybutyl-p-cresol commercially available as "BHT"; 2,2'-ethylidenebis(4,6-ditertiarybutylphenol) commercially available under the brand Isonox 129; and, octadecyl-3,5-di-t-butyl-4-hydroxybenzenepropionate.

It is a specific object of this invention to provide a stabilized polymeric composition comprising a polymer of a mono-1-olefin having incorporated therein a small but effective, stabilizing amount, sufficient to stabilize the composiition against the deleterious action of oxygen, heat and ultraviolet light, of
  (a) at least one polysubstituted piperazinone linked through a branched chain bridge to a triazine nucleus, and
  (b) at least one hindered phenol selected from the group consisting of tris(3,5-di-t-butyl-4-hydroxybenzyl)-isocyanurate; 2,6-ditertiarybutyl-p-cresol;

2,2'-ethylidenebis(4,6-ditertiarybutylphenol); octadecyl 3,5-di-t-butyl-4-hydroxybenzenepropionate commercially available as Irganox 1076; and, tris 2-[β-(3,5-di-tert-butyl-4-hydroxyphenyl)propionoxy]ethylisocyanurate, commercially available as Good-rite ®3125*.

*Good-rite is a Registered Trademark of The B. F. Goodrich Co.

It is another specific object of this invention to provide an unexpectedly effective combination of (a) an oligomer having from 2 to 10 repeating units, each one of which includes a triazine ring distally connected through the branched bridge to at least one piperazinone ring which has four lower alkyl substituents on the pierazinone ring, two on each side of the $N^4$ atom, or spiro substituents, one on each side of the $N^4$ atom, and, (b) a particular hindered phenol selected from the group consisting of Good-rite 3114; Good-rite 3125; BHT and Isonox ®129; each component (a) and (b) being present in an amount in the range from 0.1 to about 1 phr; which combination, when essentially homogeneously dispersed in a polyethylene or polypropylene film or fiber enhances both its (the film or fiber's) resistance to degradation by light, and also to heat and oxygen.

DETAILED DESCRIPTION OF PREFERRED EMBODIMENTS

The basic structure of the stabilizer compounds prepared by the synthesis described herein, is a substituted triazine ring to at least one C atom of which is attached a PSP by means of a branched bridge containing at least three atoms serially linked, the first, an N atom bound to a H atom, the N atom linked to the triazine ring, then at least two C atoms, and the N-adjacent C atom of the bridge is always disubstituted or branched (hence "branched bridge").

The manner of disubstitution is not narrowly critical provided both available bonds on the C atom are used, that is, both H atoms on the N-adjacent C atom are substituted. Though dialkyl-substituents are preferred, and most preferred are lower alkyl having from 1 to about 6 C atoms ("$C_1$–$C_6$ alkyl"), disubstitution may also be effected with a cyclized polymethylene group having from 5 to about 6 C atoms which forms a spiro cycloalkylene substituent.

Since a disubstituted N-adjacent C atom was previously thought to negate the formation of cyclized PSP, there was every reason not to disubstitute this C atom of the bridge. The relative ease of formation of the branched bridge PIP-T from conveniently available PAPA, and the concomitant economic benefit of a simpler and more effective process, was never a consideration because the reaction was not believed to be "doable". Neither was there any consideration, for the same reason, that the branched bridge compounds may have better resistance to extraction that otherwise analogous unbranched bridge PIP-T compounds.

PAPA which provide the branched bridge upon cyclization in the ketoform reaction, and a method for making such PAPA, are disclosed in U.S. Pat. No. 4,293,682 to Klueger et al, and the disclosure thereof is incorporated by reference thereto as if fully set forth herein.

The PIP-T stabilizer of this invention may be represented by the following structural formula (I):

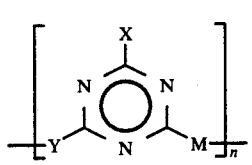
(I)

wherein,
n is an integer in the range from 1 to about 10,
said compound having functional end groups selected from H, OH and Cl when n is greater than 1;
X is a substituent having the following formula (II):

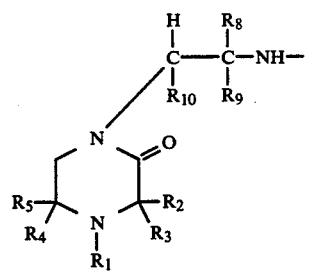
(II)

wherein,
$R_2$, $R_3$, $R_4$ and $R_5$ independently represent $C_1$–$C_{24}$ alkyl and polymethylene having from 4 to about 7 C atoms which are cyclizable forming a spiro cycloalkylene substituent with the C atom of the piperazinone ring,
$R_1$ represents hydrogen or oxygen, $C_1$–$C_{24}$ alkyl, $C_1$–$C_{12}$ hydroxyalkyl, benzyl, allyl, and $C_1$–$C_{12}$ haloalkyl;
$R_8$ and $R_9$ independently represent $C_1$–$C_{24}$ alkyl, and polymethylene having from 4 to about 7 C atoms which are cyclizable;
$R_{10}$ represents H, $C_1$–$C_6$ alkyl and phenyl;
Y may be the same as X or M;
M may be Z or Z', wherein
Z represents a radical selected from the group consisting of Cl, OH,

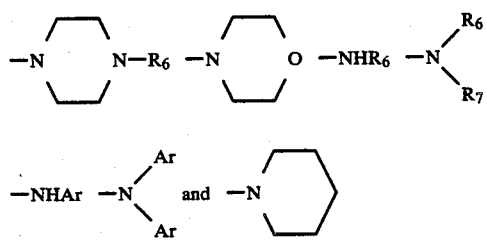

$R_6$, $R_7$ represent alkyl having from 2 to about 24 carbon atoms; and $C_4$–$C_7$ cycloalkyl;
Ar represents aryl;
Z' represents a radical selected from the group consisting of

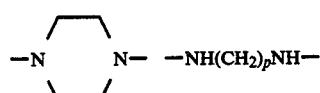

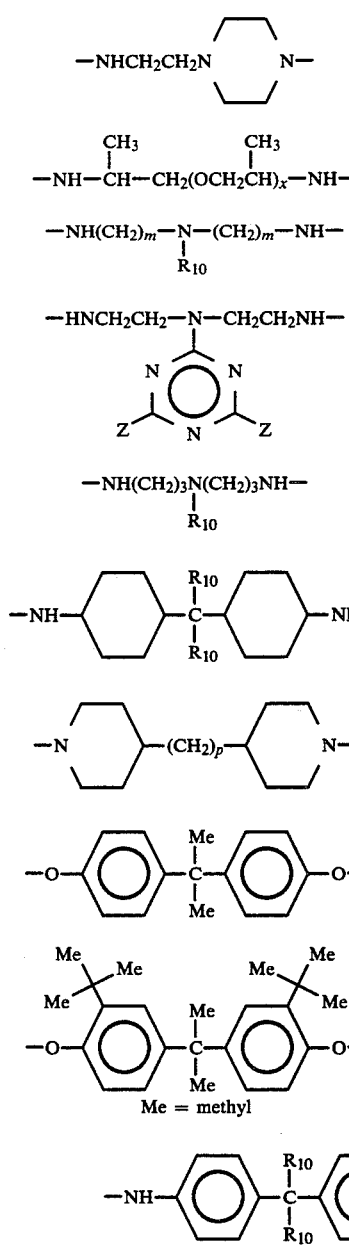

p represents an integer in the range from 2 to about 20;
x represents an integer in the range from 1 to about 50;
m represents an integer in the range from 2 to about 4 and, when n=1, Y and M may be he same as X.

Particular monomeric PIP-T compounds of this invention may be represented by the following formula (III):

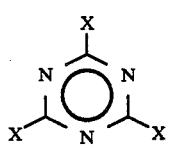

wherein,
X has the same connotation as hereinabove.

Other monomeric PIP-T compounds of this invention may be represented by the following formula (IV):

wherein,
X and Z have the same connotation as hereinabove.

Particular PIP-T bis-compounds of this invention may be represented by the following formula (V):

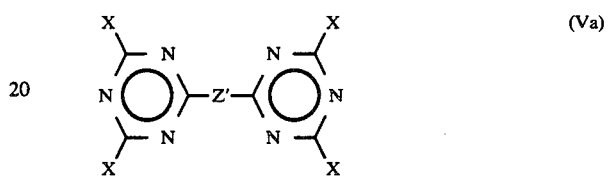

and

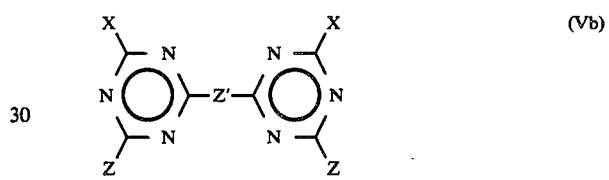

wherein,
X, Z and Z' have the same connotation as hereinabove.

Still other PIP-T compounds are oligomers of the substituted triazine ring, and may be represented by the following formula (VI):

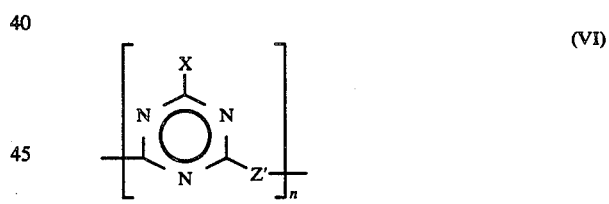

wherein,
an oligomer is terminated with functional end groups selected from H, OH and Cl, and
X, Z' and n have the same connotation as hereinabove.

Still other PIP-T compounds are PAPAs having pendant triazine nuclei attached to the PAPA's N atoms, and each triazine nucleus distally connected to a PSP, represented by the following structure (VII):

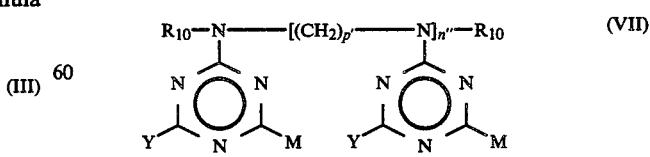

wherein,
p' is an integer in the range from 2 to 8;
n" is an integer in the range from 2 to 12. and, Y and M have the same connotation as hereinabove.

In monomeric PIP-T compounds, Z and Z' each includes a terminal functional group selected from H, lower $C_1$–$C_6$ alkyl, and $C_1$–$C_5$ lower hydroxyalkyl.

It is especially significant that these relatively high molecular weight (mol wt) compounds contain a branched bridge which distally links the PSP to a triazine moiety, and each, namely the PSP, the triazine and the bridge may independently be substituted with a variety of substituents to produce stabilizers having not only desirable uv light stabilizing properties, but also heat and oxidation stabilizing properties, complemented with suitable solubility and dispersability.

The substituted PIP-T compounds are generally oils or solids, and soluble or partially soluble in acetone, diethyl ether, dioxane, tetrahydrofuran, carbon tetrachloride, chloroform, lower primary alcohols having from 1 to about 5 C atoms such as methanol, ethanol and propanol, aromatic hydrocarbons such as benzene and toluene, but much less soluble in aliphatic hydrocarbons such as hexane. Substituted PIP-T compounds are generally insoluble in water; they range in color from white to yellow, when pure.

The amount of stabilizer employed will vary with the particular material to be stabilized and also the substituted branched PIP-T employed. Generally however, for effective uv light stabilization of organic materials, an amount of the PIP-T used is in the range from about 0.001 percent to about 10 percent by weight (% by wt) based on the weight of organic material. In typical stabilized compositions the amount of branched bridge PIP-T used is in the range from about 0.01 to about 5% by wt.

Compositions of this invention are synthetic resinous materials which have been stabilized to combat the deleterious effects of uv light, thermal or oxidative degradation such as are usually evidenced by discoloration and/or embrittlement. These compositions generally benefit from the inclusion of additional, secondary stabilizers to achieve even greater stability against a combination of actinic light, heat and oxygen. Therefore, in conjunction with the stabilizers of this invention, compositions may include stabilizers against degradation by heat and/or oxygen which secondary stabilizers may be present in the range from about 0.1 part to about 10 parts by wt, and preferably from about 0.2 part to about 5 parts by wt per 100 parts by wt of the organic continuous phase. Several types of known UV secondary stabilizers may be used, such as those disclosed in U.S. Pat. Nos. 3,325,448; 3,769,259; 3,920,659; 3,962,255; 3,966,711; 3,971,757; inter alia.

Organic materials which may be stabilized against uv light, thermal and oxidative degradation, include copolymers of butadiene with acrylic acid, alkyl acrylates or methacrylates, polyisoprene, polychloroprene, and the like; polyurethanes; vinyl polymers known as PVC resins such as polyvinyl chloride, copolymers of vinyl chloride with vinylidene chloride, copolymers of vinyl halide with butadiene, styrene, vinyl esters, and the like; polyamides such as those derived from the reaction of hexamethylene diamine with adipic or sebacic acid; epoxy resins such as those obtained from the condensation of epichlorohydrin with bisphenols, and the like; ABS resins, polystyrene, polyacrylonitrile, polymethacrylates, polycarbonates, varnish, phenol-formaldehyde resins, polyepoxides, polyesters, and polyolefin homo- and copolymers such as polyethylene, polypropylene, ethylene-propylene polymers, ethylene-propylenediene polymers, ethylene-vinyl acetate polymers, and the like. The substituted PIP-T compounds can also be used to stabilize mixtures and blends of polymeric materials such as ABS resin blends, PVC and polymethacrylate blends, and blends of polyolefin homopolymers and copolymers such as blends of polypropylene in EPDM polymers.

Most particularly, branched bridge PIP-T compounds of this invention having at least one 3,3,5,5-tetraalkyl piperazinone distally linked to a triazine ring, most preferably with additional substituents at one or both of the remaining substitutable positions on the triazine ring, are especially useful as uv-light-stabilizers for synthetic resinous materials which are at least partially permeable to visible light, and particularly for those which are transparent thereto, such as the polyvinylaromatics and polyolefins.

Many known compounding ingredients may be used along with the substituted PIP-T stabilizers in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, castor oil, tall oil, glycerin, and the like.

Particularly desirable secondary stabilizers are one or more antioxidants used in the range from about 0.1 part to about 20 parts by weight, preferably from about 0.2 part to about 5 parts by weight per 100 parts by weight of the material. Of the types of antioxidants to be used, are phosphite, phosphate, sulfide and phenolic antioxidants, the last being preferred. Most preferred are the hindered phenol AOs specified hereinabove, though others are also useful, such as 2,6-di-t-butyl-paracresol; 2,2'-methylene-bis(6-t-butyl-phenol); 2,2'-thiobis(4-methyl-6-t-butyl-phenol); 2,2'-methylene-bis-(6-t-butyl-4-ethylphenol); 4,4'-butylidene-bis(6-t-butyl-m-cresol); 2-(4- hydroxy-3,5-di-t-butylanilino)-4,6-bis-(octylthio)-1,3,5-triazine; benzenepropanoic acid, 3,5-bis(1,1-dimethylethyl)-4-hydroxy-(2,4,6-trioxo-1,3,-5-triazine-1,3,5(2H,4H,6H)--triyl)tri-2,1-ethanediyl ester (Good-rite ®3125); tetrakis[methylene 3-(3',5'-di-t-butyl-4'-hydroxyphenyl)propionate]methane; and particularly commercially available antioxidants such as Irganox 1010, 1035, 1076 and 1093. Other ingredients such as pigments, tackifiers, flame retardants, fungicides, and the like may also be added.

The branched bridge PIP-T stabilizers, and the other compounding ingredients if used, can be admixed with organic materials using known mixing techniques and equipment such as internal mixing kettles, a Banbury mixer, a Henschel mixer, a two-roll mill, an extruder mixer, or other standard equipment, to yield a composition which may be extruded, pressed, blowmolded or the like into film, fiber or shaped articles. Usual mixing times and temperatures can be employed which may be determined with a little trial and error for any particular composition. The objective is to obtain intimate and uniform mixing of the components. A favorable mixing procedure to use when adding a substituted PIP-T to an organic material is either to dissolve or suspend the compound in a liquid such as methylene chloride before adding it, or to add the PIP-T directly to the polymeric organic material whether the PIP-T is in the form of a powder or oil, or to extruder-mix the PIP-T and the polymeric material prior to forming the product.

The uv stability of a particular composition containing a polymeric material and a branched bridge PIP-T can be evaluated by exposing a prepared sample of the composition to Xenon or carbon arc light in a Weather-O-meter (ASTM D2569-79) operating at a temperature of about 145° F. (63° C.) at about 50% relative humidity. Degradation of the sample is followed by periodically measuring the tensile strength after exposure, and the hydroperoxide absorption band at 3460 cm$^{-1}$ or carbonyl absorption band at 1720 cm$^{-1}$ using an IR spectrophotometer. The rapid formation of carbonyl indicates failure of the sample. The test procedure is well known, and is published in the text *Photodegradation, Photo-oxidation and Photostabilization of Polymers* by Ranby and Rabek, John Wiley & Sons, N.Y., N.Y. (1975), at pages 129 et seq., and is disclosed in U.S. Pat. No. 3,909,493. Failure of the sample is also checked by visual signs of cracking when the sample is bent 180°. Degradation of fibers is checked by suspending lengths of fiber spaced about 0.125" apart on a stainless steel holder and testing three of them periodically until they suffer a 50% loss of initial tensile strength (ASTM D2343-67).

Samples of the compositions are also checked for oxidative and thermal stability by measuring the time to discoloration and/or embrittlement of the sample after aging in an air circulating oven at 125° C. (ASTM D1204-78), and other standard tests. These tests include tests for resistance to water extraction, perchloroethylene extraction, and "gas fade" as will be explained in greater detail hereinafter.

Preparation of polysubstituted piperazinone ("PSP")

In a typical preparation, the PSP is prepared by the ketoform synthesis, with or without a phase transfer catalyst. This synthesis is generally carried out with 1,2-diamines having TFPA groups. These diamines are reacted with a saturated or unsaturated monoketone and certain aromatic aldehydes such as benzaldehyde, along with a haloform reactant, in an organic solvent for the reactants, in the presence of aqueous or solid alkali. Though a phase transfer catalyst accelerates the reaction, it is found to proceed quite well even without it, provided the carbonyl reactant is a ketone and it is present in large excess. By large excess we refer to an amount in the range from 2 to 20 times the theoretical amount required. The reaction with a ketone proceeds at room temperature or below, though it may also be carried out at elevated temperatures, depending upon the particular other reactants present. A preferred temperature range is from about $-10°$ C. to about 30° C.

Preferred ketones are aliphatic monoketones having from 3 to about 12 carbon atoms, and cyclic monoketones having from about 5 to about 8 carbon atoms. Most preferred are the lower aliphatic ketones such as acetone including those having up to about 12 carbon atoms, and the cycloaliphatic ketones such as cyclohexanone which may be substituted.

A particular PSP is conveniently synthesized from N$^1$-(2-amino-2-methylpropyl)-2-methyl-1,2-propanediamine (identified herein as TFPA(1)" for brevity), as described hereinbelow. The PSP formed is 1-(2-amino-2-methylpropyl)-3,3,5,5-tetramethylpiperazinone having the following structure:

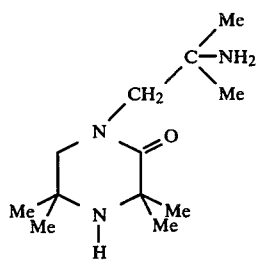

PSP(VIII)

In a 5 liter three-necked flask were placed 1137.1 g (19.6 moles) of acetone, 269.5 g (2.26 moles) of CHCl$_3$, and 267.8 g (1.5 moles) of 89% pure TFPA(1). To this cooled and stirred mixture was added at intervals, aliquots of NaOH until 295.2 g (7.38 moles) were added over a period of 3 hr while maintaining the temperature of the flask in the range from $-3°$ to 6° C.

After reacting overnight at $-4°$ C., the resulting white slurry was filtered. The filtrate and an acetone wash of the white cake were stripped to obtain 383.3 g of straw-colored liquid (75.1% yield). The crude product was distilled in a 4" diam column in the presence of NaOH. The desired product boils at 110°-2° C./0.5 mm Hg, and 240.2 g of 96% pure PSP was isolated.

It is important to note that the TFPA(1) used in the foregoing preparation has terminal free primary amine groups, but a disubstituted ("branched") C atom next to each terminal free primary amine group, as seen in the following structure:

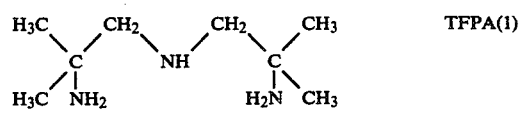

TFPA(1)

which is one preferred embodiment of the general structure:

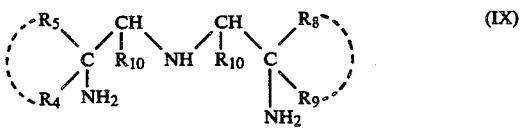

(IX)

In the '092 patent, though the general structure for a reactive PAPA showed terminal free primary amine groups, such an amine with one unbranched C atom adjacent a terminal free primary amine group, fails to produce the desired cyclized product with any directivity. Therefore, one TFPA in the '092 preparation was substituted, so as to negate its reactivity. The amine with the substituted amine group is N-(2-butyl)-N'-(2-amino-2-methylpropyl)-1,2-ethanediamine which has the structure:

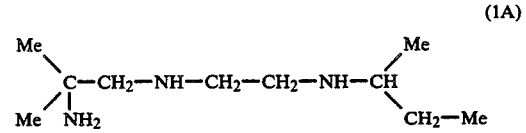

(1A)

Preparation of 1-[2-[(4,6-dichloro-1,3,5-triazine-2-yl)amino]-2-methylpropyl]-3,3,5,5-tetramethylpiperazinone]: identified herein as "PIP-T(1)" for brevity.

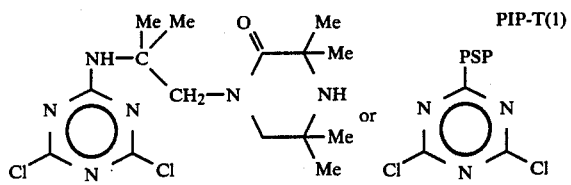

In a 3 liter three-necked flask were placed 266.2 g (1.40 mole) of cyanuric chloride and 900 ml of toluene. To this cooled and stirred slurry was added dropwise 338. 6 g (1.4 mole) of 94% pure PSP in 150 ml of toluene over a period of about 1.5 hr, while maintaining the flask temperature in the range −3° to 3° C. This is followed by the addition of 61.6 g of NaOH in 246 ml water. The addition took 1.25 hr. After reacting 2 hr at −1° to 5° C., the resulting slurry was filtered to isolate an off-white solid. After washing with hexane, then with water, the solid was dried to isolate 378.9 g of off-white solid (99% pure by GC analysis).

The yellow filtrate was washed twice with water (2×700 ml), dried over Na₂SO₄, filtered and stripped to obtain 128.8 g of light yellow solid. This crude product was washed with a mixture of 300 ml hexane and 70 ml toluene, and dried to isolate 110.1 g of off-white solid (98% pure by GC). The combined crops weighed 489.0 g (93% yield), mp 123°-6° C. The above structure is supported by field desorption (FD) infrared (IR) and nuclear magnetic resonance (nmr) spectroscopy.

Preparation of 1-[2-[[4-chloro-6-(cyclohexylamino)-1,3,5-triazine-2-yl]amino]-2-methylpropyl]-3,3,5,5-tetramethylpiperazinone: identified herein as PIP-T(2)

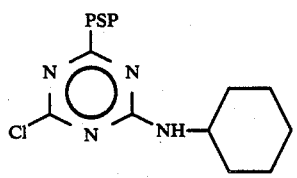

In a 100 ml three-necked flask were placed 7.51 g (0.020 mole) of PIP-T(1) prepared as described hereinabove, and 70 ml toluene. To the above stirred solution was added dropwise 1.98 g (0.02 mole) of cyclohexylamine in 5 ml toluene over a period of about 3 min. A mild exotherm raises the temperature from 23° C. to 39° C. After cooling to 28° C. with a water bath, 0.9 g of NaOH in 6 ml water is added dropwise, over a period of a couple of min.

A thin white to gray slurry formed while the flask temperature rose from 28° C. to 31° C. About 80 min later, the reaction mixture was placed in a 500 ml separatory funnel and washed with 100 ml water. The organic layer was washed a second time with 100 ml water, yielding a white solid. The mixture was filtered to isolate the white solid which was again washed with 100 ml water, filtered and dried to obtain 6.94 g of the PIP-T(2) product (79.2% yield), mp 124°-9° C. The structure was confirmed by FD, IR, and nmr spectroscopic analysis. One-pot preparation of PIP-T(2) from N¹-(2-amino-2-methylpropyl)-2-methyl-1,2-propanediamine and 1-(2-amino-2-methylpropyl)-3,3,5,5-tetramethylpiperazinone:

In a 2 liter three-necked flask were placed a 377.5 g (6.5 moles) of acetone, 89.5 g (0.75 mole) of CHCl₃, and 80.4 g (0.5 mole) of N¹-(2-amino-2-methylpropyl)-2-methyl-1,2-propanediamine. To this cooled mixture was added aliquots of NaOH until 94.0 g have been added over a period of about 2 hr while maintaining the flask temperature at −4° to 3° C.

After reacting 3 hr at −2° to 9° C., 89.3 g (0.47 mole) of cyanuric chloride was added in aliquots to the above slurry, during which time the reaction temperature rose to 12° C. over a period of about 30 min. This is followed the addition of 20 g of NaOH in 80 ml of water. The addition took about 20 min.

After reacting 70 min, 37.2 g (0.375 mole) of cyclohexylamine in 100 ml of acetone was added dropwise over a period of about 15 min. Then 100 g of 20% aqueous NaOH solution was added dropwise within 10 min. During these additions the maximum flask temperature was 12° C.

The reaction was allowed to proceed overnight at room temperature. The resulting light yellow solid (47.0 g) was isolated by filtration, washing and drying. It was 100% pure confirmed by GC analysis and had a mp 124°-9° C.

Additional product was obtained from the original filtrate by adding 1.2 liters of water and stirring. Within about 5 min a gummy solid is formed which was further washed with water and filtered. A light straw-colored solid was obtained which was dried overnight and ground to obtain 109.5 g which was recrystallized from toluenehexane to obtain 67.6 g of solid (99% pure by GC).

The above filtrate was concentrated to about 40 ml of slurry and filtered. The solid was titrated in hexane, filtered and air dried to isolate 31.5 g of light tan solid. This solution was recrystallized from hexane-acetone to obtain 20.6 g of PIP-T(2) which was found to be 98.5% pure by GC analysis. The total amount of product obtained was 135.2 g (61.7% yield).

Particular monomeric PIP-Ts having a single triazine nucleus are illustrated by compounds having the following structures:

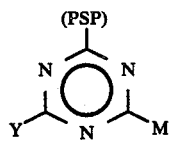

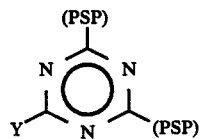

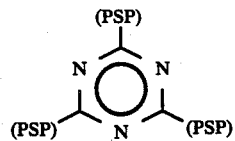

wherein (PSP) has the structure:

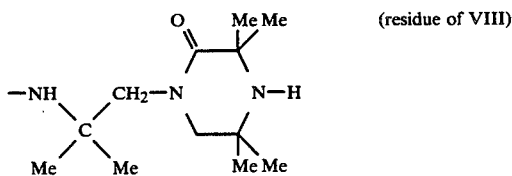 (residue of VIII)

and Y and M have the following structures:

| Compound identif. | Y | M |
|---|---|---|
| PIP-T(3)1 | ![N-(cyclohexyl)2] | OH |
| PIP-T(3)2 | N—[CH$_2$CH(Et)C$_4$H$_9$]$_2$ | N—[CH$_2$CH(Et)C$_4$H$_9$]$_2$ |
| PIP-T(3)3 | NH-cyclohexyl | NH-cyclohexyl |
| PIP-T(3)4 | N—(CH$_2$—CH=CH$_2$)$_2$ | N—(CH$_2$—CH=CH$_2$)$_2$ |
| PIP-T(3)5 | N—(CH$_2$—CH=CH$_2$)$_2$ | OH |
| PIP-T(3)6 | NHC$_{12}$H$_{25}$ | NHC$_{12}$H$_{25}$ |
| PIP-T(3)7 | NHC$_{12}$H$_{25}$ | NH-cyclohexyl |
| PIP-T(4)1 | N(C$_4$H$_9$)$_2$ | |
| PIP-T(4)2 | NH-cyclohexyl | |
| PIP-T(4)3 | NH—CH$_2$CH(Et)C$_4$H$_9$ | |
| PIP-T(4)4 | N—(CH$_2$—CH=CH$_2$)$_2$ | |
| PIP-T(4)5 | NHC$_{12}$H$_{25}$ | |

Whether the triazine ring is mono- di- or tri-substituted with a PSP depends upon the moles of PSP reacted with cyanuric chloride under conditions analogous to those set forth in the '092 patent.

Particular bis-triazine PIP-Ts having two triazine nuclei interconnected by an amine bridge are illustrated by compounds having the following structures:

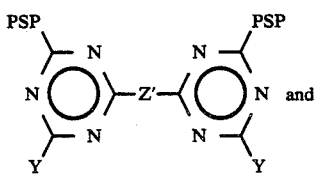 PIP-T(6)

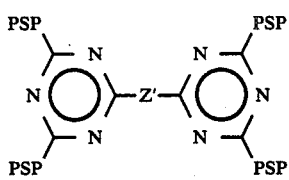 PIP-T(7)

wherein PSP, Y and Z' have the connotations set forth hereinbelow.

| Compound identif. | Y | Z' |
|---|---|---|
| PIP-T(6)1 | NH-cyclohexyl | —N(piperazine)N— |
| PIP-T(6)2 | N-(cyclohexyl)$_2$ | " |
| PIP-T(6)3 | N(Et)-cyclohexyl | " |
| PIP-T(6)4 | NHCH$_2$CH(Et)C$_4$H$_9$ | " |
| PIP-T(6)5 | N(C$_4$H$_9$)$_2$ | " |
| PIP-T(7)1 | | " |
| PIP-T(7)2 | | NH(CH$_2$)$_6$NH |

Other PSPs of this invention are represented by:

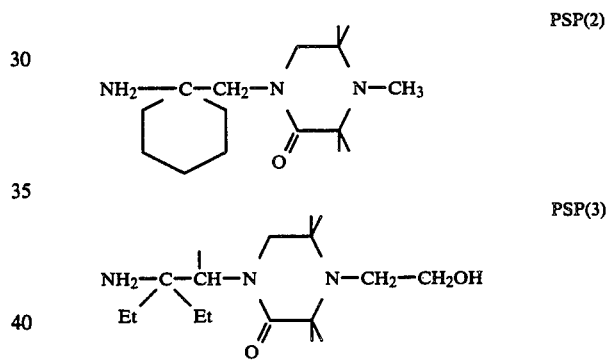

Preparation of a "pendant PIP-T" in which a "main chain PAPA" is provided with a PIP-T susbstituent on every N atom in the PAPA's main chain (so termed to avoid confusion with the branched PAPA):

A pendant PIP-T having from 3 to 6N atoms in the PAPA chain, and from 2 to 3C atoms intermediate each N atom in the chain, may be prepared by reaction of an appropriate TFPA with a PIP-T having a reactive leading group which will react so as to substitute one H atom bound to an amine N atom in the PAPA chain. The result is a pendant PIP-T having a PIP-T substituent on each N atom of the PAPA. The general structure of a PAPA used to form the pendant PIP-T is:

 (X)

wherein, R$_{11}$ represents H, C$_1$–C$_{24}$ alkyl, C$_4$–C$_7$ cycloalkyl, or C$_1$–C$_{12}$ hydroxyalkyl; p' is either 2 or 3; and n" is an integer in the range from 2 to about 12.

The general structure of the pendant PIP-T formed as:

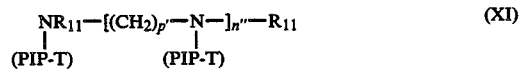 (XI)

A particular pendant PIP-T in which the substituent is PIP-T(2) and the PAPA is N¹-(2-aminoethyl)-1,2-ethanediamine, is identified as "P[PIP-T(2)]" and represented as follows:

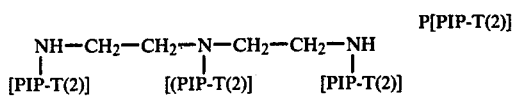

wherein [PIP-T(2)] is the residue of PIP-T(2).

The structure of the P[PIP-T(2)], more fully identified as 1,1'-[[[4-(cyclohexylamino)-6-[[1,1-dimethyl-2-(3,3,5,5-tetramethyl-2-oxo-1-piperazinyl)ethyl]amino]-1,3,5-triazin-2-yl]imino]bis[2,1-ethanediylimino[6-(cyclohexylamino)-1,3,5-triazine-4,2-diyl]imino(2,2-dimethyl-2,1-ethanediyl]]]bis[3,3,5,5-tetramethyl-piperazinone], is as follows:

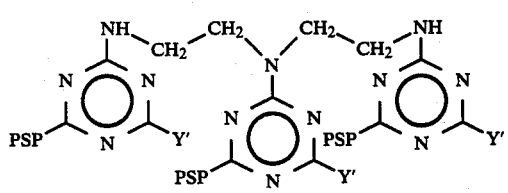

(XII)

In a 845 ml reactor were charged 13.14 g (0.03 mole) of PIP-T(2), 1.03 g (0.01 mole) of N¹-(2-aminoethyl)-1,2-ethanediamine, 1.44 g NaOH in 5.8 ml of water, and 400 ml xylenes. After reacting the mixture for 18 hr at 210° C., the reaction mass was cooled and washed twice with water (2×350 ml). The organic layer was separated, dried over Na₂SO₄, filtered and stripped to obtain about 50 ml of yellow oil. Addition of about 220 ml hexane to the oil with stirring gave a slurry from which 9.99 g (76.5% yield) of an off-white solid was isolated, mp 120°-5° C. The above structure was confirmed by mass spectra analysis.

In the foregoing P[PIP-T(2)] the connotation of PSP is the same as before, and Y' represents the structure:

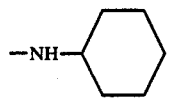

In a manner analogous to that described immediately hereinabove, the following P[PIP-T]s were prepared starting from an appropriate PAPA. The structures are as follows:

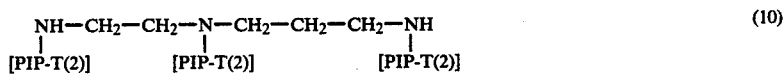 (10)

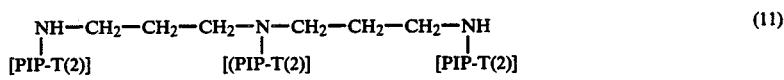 (11)

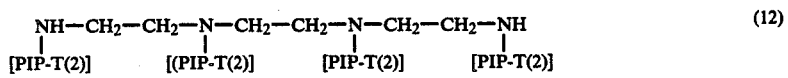 (12)

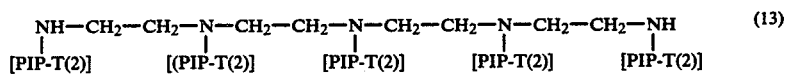 (13)

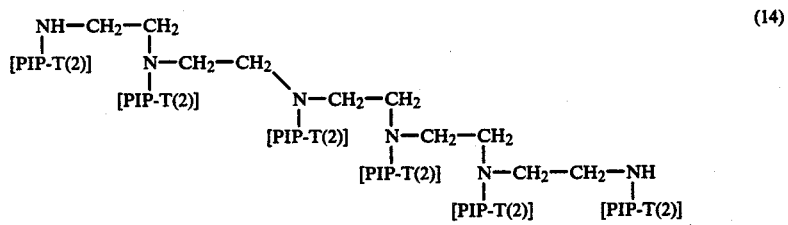 (14)

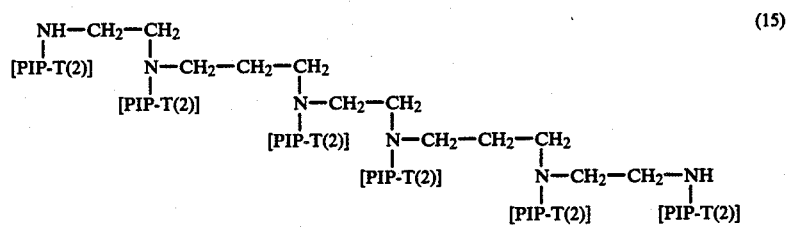 (15)

As will readily be ascertained, the mol wts of the monomeric PIP-T compounds with a single triazine nucleus may be calculated from their structural formulae. The mol wt of such a monomeric PIP-T may be increased by changing the substituents on the piperazinone ring, as well as those on the substitutable atoms of the branched bridge. The mol wt can further be greatly increased by forming P[PIP-T]s from the PIP-T and an appropriate PAPA.

Commercially available PAPAs which lend themselves to the preparation of P[PIP-T]s are generally available as mixtures of chains having from 3 to about 6 amine groups, and the terminal groups are primary or secondary amines. With as many as 6N atoms, every N atom is substituted with a PIP-T, but with more amine groups in a PAPA, not all the N groups are substituted. Thus commercially available polyethyleneimines having a mol wt in the range from 600 to about 100,000 may be substituted with PIP-Ts, under analogous reaction conditions, but with considerably greater difficulty. It will be evident that the mol wt of a P[PIP-T] can be computed from its structure, and the structure may be modified to provide a desired mol wt. The mol wts of P[PIP-T]s may also be determined with a vapor pressure osmometer which provides a number average mol wt ($\overline{Mn}$). The mol wt may also be obtained by mass spectrographic analysis, and if the mol wt is above about 4000, gel permeation chromatography may be used.

Several PSP and PIP-T compounds, with either unbranched bridge or branched bridge structures, were prepared and tested. Prior art unbranched bridge PSP compound 2A and PIP-T compound 8A of the '092 patent were compared to corresponding branched bridge compounds. The structures of some of the compounds prepared are given below:

PSP 2A of '092 patent:

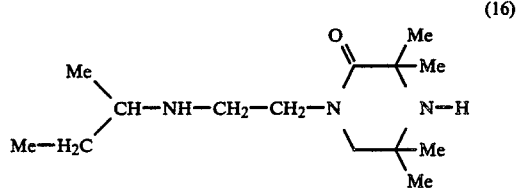

(16)

PIP-T 8A of '092 patent:

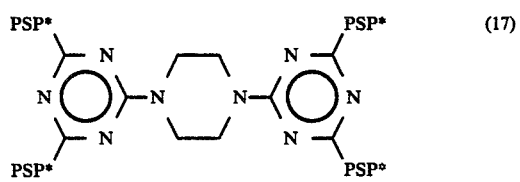

(17)

wherein

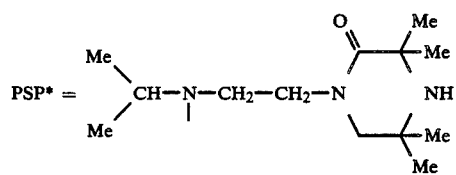

It will be realized that no P[PIP-T] will be formed with PIP-T(5); and, that when Y is Cl in PIP-T(4), the P[PIP-T] formed will have a triazine ring which is di-PSP-substituted. P[PIP-T]s formed with PIP-T(3) require that either Y or M be Cl. Thus, a wide array of P[PIP-T]s may be prepared in which not only can the main chain PAPA be varied, but the substituents on both the triazine ring and the PSP can be independently chosen to give the P[PIP-T] a wide range of properties, some more desirable than others.

Particular P[PIP-T]s are formed with various PIP-T(3) compounds in which the triazine ring has one PSP substituent, and one of M or Y is retained. In the PIP-T(3) reactant to be used to form the P[PIP-T], if M is retained then the other is Cl which is eliminated upon reaction. The P[PIP-T] formed with PIP-T(3) is represented by:

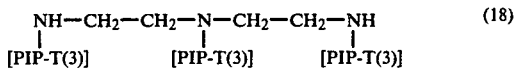

(18)

Particular P[PIP-T]s are formed with various PIP-T(4) compounds in which the triazine ring has two PSP substituents and the Y (which is replaced with Cl prior to the reaction) is eliminated upon reaction. The P[PIP-T] formed has a structure analogous to that given hereinabove and is represented by:

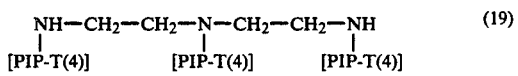

(19)

wherein the triazine nucleus in [PIP-T(4)] is di-substituted with a desired PSP.

Particular P[PIP-T]s prepared from triethylene-tetramine as the main chain PAPA in a manner analogous to that described hereinabove, are represented by the structures:

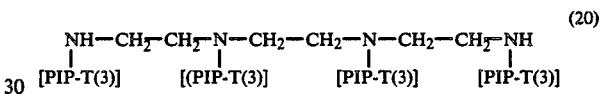

(20)

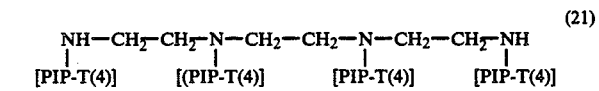

(21)

A particular P[PIP-T] derived from 3,3'-iminobis-propylamine has the structure

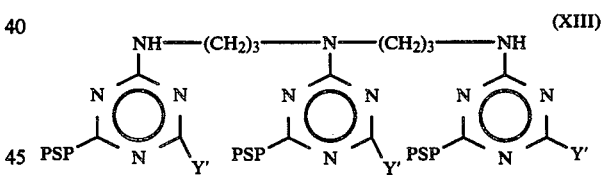

(XIII)

The foregoing P[PIP-T]s are simply illustrative of various compounds which have been prepared. A wide range of analogous compounds may be prepared in a similar manner, and tested to determine which particular compounds have the most desirable properties. In addition to the foregoing P[PIP-T]s other compounds having the general formula (VII) hereinabove may be prepared in which Y and M may be the same or different and is selected from the group consisting of X (PSP), —NHC$_{12}$H$_{25}$; —N—(C$_2$H$_5$)$_2$;

—NHC$_{12}$H$_{25}$; —N—(C$_2$H$_5$)$_2$; —N—(C$_4$H$_9$)$_2$; —N—(C$_3$H$_7$)$_2$;

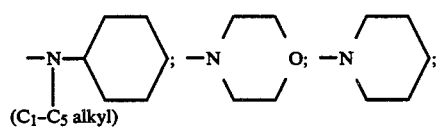

-continued

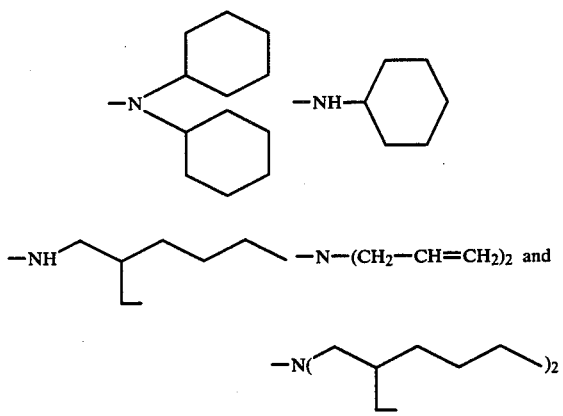

The PIP-Ts and P[PIP-T]s are incorporated in a polymer in conventional ways for example by hot milling so the stabilizer is substantially homogeneously dispersed in the polymer before it is subsequently extruded, injection molded, compression molded or blow molded and the like into any desired shaped articles, especially fiber and film. Where the polymer is prepared from a liquid monomer as in the case of styrene, the stabilizer may be dispersed or dissolved in the monomer prior to polymerization or curing.

In addition to the secondary stabilizers including thermal AOs, disclosed hereinabove, the stabilized polymer composition may contain other additives such as plasticizers, pigments, fillers, dyes, glass or other fibers, and the like. Since, in many applications, the polymer is pigmented or dyed and is therefore particularly susceptible to actinic and thermal degradation, it is conventional to incorporate sufficient thermal AO and PS to protect the polymer during its useful life, the AO and PS each being used in an amount in the range from about 0.01% to about 3% by wt.

An illustrative preparation of P[PIP-T]s from a commercially available tetraethylenepentamine (TEPA) main chain PAPA provides a mixture of P[PIP-T]s. The preparation is as follows:

22.12 g (0.0505 mole) of PIP-T(2) and 1.89 g (0.01 mole) of TEPA are dissolved in 160 ml toluene, and 2.4 g of NaOH in 9.6 ml water are added to a 300 ml autoclave and the reaction is carried out at 220° C. for 10 hrs. The reaction mass is cooled and washed with water three times (150 ml each wash). The toluene layer is stripped and a solid crude is obtained.

Upon working up the mass it is found that about 80% is a P[PIP-T] formed with a TEPA main chain, 10% is formed with a triethylenetetramine main chain, and 10% is formed with a pentaethylenehexamine main chain. The structure of the P[PIP-T] formed from the TEPA component is given hereinabove; its m pt is 160° C.

The foregoing compounds are tested for activity as antioxidants and photostabilizers by incorporating 0.2 phr of the stabilizer in various polymers. The tests set forth hereinbelow are with polypropylene. Photostabilization is tested in a Xenon Weather-O-Meter in accordance with ASTM D2565-83; oven aging is conducted in a modified ASTM D1204-78 procedure; tensile testing of 20 mil thick compression molded plaques or dumbells is done according to ASTM D882-83 (Method A); and tensile testing of fibers is done according to ASTM D3822-79.

Resistance to extraction with hot water is tested by incorporating 0.2 phr of the stabilizer in polypropylene which is extruded into 0.2 mil thick tape. A piece of the tape is suspended in a bath of boiling water for 24 hrs, removed from the bath and placed in the Weather-O-Meter for testing. The results are compared with those obtained for another piece of tape (with the same stabilizer, 0.2 phr) which tape was not subjected to extraction before it was tested in the Weather-O-Meter. Preparation of an oligomer containing a PIP-T moiety:

The oligomer having the structure set forth hereinbelow is conveniently prepared by the reaction of PIP-T(1) with a suitable diamine as is illustrated as follows

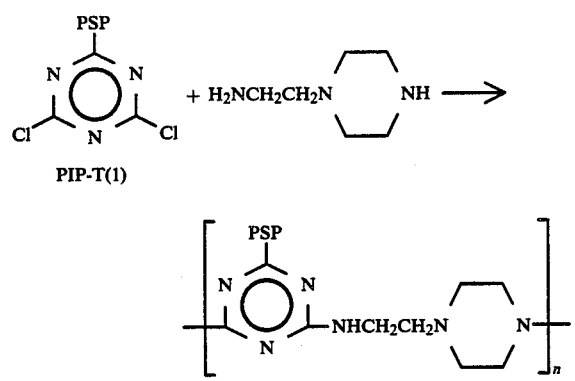

The oligomer is identified as poly[[6-[[1,1-dimethyl-2-(3,3,5,5-tetramethyl-2-oxo-1-piperazinyl)ethyl]-amino]-1,3,5-triazine-2,4-diyl]imino-1,2-ethanediyl-1,4-piperazinediyl].

The foregoing reaction is carried out with 15.01 g of PIP-T(1) and 5.30 g of 1-(2-aminoethyl)piperazine (equimolar amounts) in 400 ml of xylene to which 4 g of NaOH in 16 ml water are added, all placed in a 845 ml autoclave. The reaction is carried out at 170° C. for about 10 hr after which time the reaction mixture is cooled and filtered to yield a light brown solid. The solid is worked up and recovered as an off-white solid the structure of which, confirmed by nmr and IR analyses, is found to be that given above.

Representative compounds identified by code hereinbefore are illustrated hereunder by structure and proper identification for the sake of greater clarity.

For example PIP-T(4)2 has the structure:

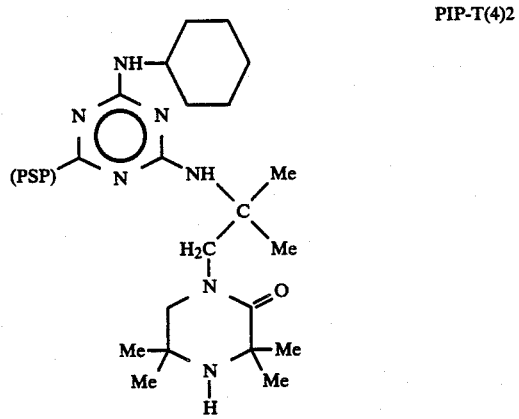

PIP-T(4)2 and is identified as: 1,1'-[(6-cyclohexylamino-1,3,5-triazine-2,4-diyl)bis[imino(2,2-dimethyl-2,1-ethanediyl)]]-bis[3,3,5,5-tetramethylpiperazinone].

The related compound PIP-T(4)3 has the structure:

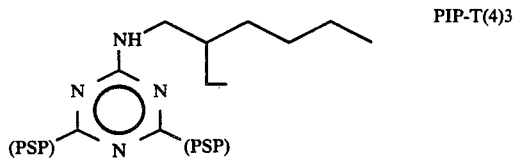

and is identified as: 1,1'-[6-(2-ethylhexyl)amino-1,3,5-triazine-2,4-diyl]bis[imino(2,2-dimethyl-2 1-ethanediyl)]]-bis[3,3,5,5-tetramethylpiperazinone].

A PIP-T with a single PSP substituent, such as PIP-T(3)3 is represented by the structure:

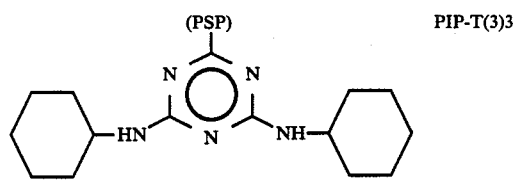

and is identified as: 1-[2-[[4,6-di(cyclohexylamino)-1,3,5-triazin-2-yl]amino]-2-methylpropyl]-3,3,5,5-tetramethylpiperazinone.

The compound PIP-T(7)1 is represented by the structure:

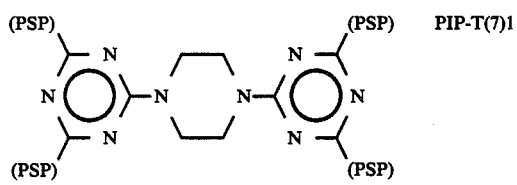

and is identified as: 1,1',1'',1'''-[1,4-piperazinediyl-bis[1,3,5-triazine-6,2,4-triylbis[imino(2,2-dimethyl-2,1-ethanediyl)]]]tetrakis[3,3,5,5-tetramethylpiperazinone].

The related compound PIP-T(7)2 is identified as: 1,1',1'',1'''-[1,6-hexanediylbis[imino-1,3,5-triazine-6,2,4-triylbis[imino(2,2-dimethyl-2,1-ethanediyl)]]]tetrakis[3,3,5,5-tetramethylpiperazinone].

Table I herebelow sets forth data obtained in oven aging and photostabilization tests conducted with yarn made of Profax 6301 polypropylene which consists of 40 filaments (approx 10 denier) for a total of 400–500 denier per yarn. Each piece of yarn (or 'fiber') including the blank, contained 0.1 part Ca stearate per 100 parts resin (phr), and 0.2 phr of PS which is identified.

Oven aging is done at 125° C. in a convection oven in a conventional manner except that samples are rotated manually, daily. In this oven aging test, loops of yarn are suspended in an oven which substantially meets the requirements of ASTM D3012-79. A loop is removed from the oven every couple of days and tested for tensile strength. When the tensile is one-half (½) the original tensile, the sample is deemed to have failed.

Photostabilization is measured by Xenon Weather-O-Meter tests conducted with samples each of which consists of 30 or 40 slightly spaced-apart turns of filament on a stainless steel holder. A 2" long piece of fiber (in triplicate) is removed every 300 hr and tested for tensile. When the tensile is ½ the original tensile, the sample is deemed to have failed.

Chimassorb 944 is a commercially available polytriazine having piperidine substituents, disclosed in U.S. Pat. No. 4,086,204. The PIP-T with the unbranched bridge is made according to the disclosure in U.S. Pat. No. 4,480,092, and is tested for comparison purposes.

TABLE I

| Stabilizer used | Xenon W'er-O-Meter (hr) | Oven Aging (days) |
|---|---|---|
| Blank, no stabilizer | 24 | 1 |
| PIP-T(3)1 | 1250 | 14 |
| PIP-T(3)3 | 1430 | 5 |
| PIP-T(3)6 | 780 | 8 |
| PIP-T(3)7 | 1100 | 5 |
| PIP-T(4)2 | 1120 | 5 |
| PIP-T(6)1 | 1260 | 5 |
| PIP-T(6)3 | 1210 | 6 |
| PIP-T(6)4 | 960 | 5 |
| PIP-T(7)1 | 1120 | 5 |
| XII (Y' = N(C$_4$H$_9$)$_2$ | 1260 | 11 |
| XII (Y' = —N(CH$_3$)(cyclohexyl)) | 1380 | 5 |
| XII (Y' = NH—CH$_2$CH(C$_2$H$_5$)C$_4$H$_9$) | 1040 | 5 |
| XII (Y' = —N(C$_2$H$_5$)(cyclohexyl)) | 1170 | 5 |
| XII ("P[PIP-T(2)]") | 940 | 5 |
| XII (Y' = —N(piperidinyl)) | 1390 | 12 |
| XII (Y' = —HN(cyclohexyl)) | 1290 | 8 |
| XIII (Y' = —N(C$_4$H$_9$)$_2$ | 1310 | 5 |
| XIII (Y' = —N(CH$_3$)(cyclohexyl)) | 1340 | 5 |
| XIII (Y' = —N(morpholinyl O)) | 1230 | 7 |
| XIII (Y' = NH—CH$_2$CH(C$_2$H$_5$)C$_4$H$_9$) | 1010 | 9 |
| XIII (Y' = —N(C$_2$H$_5$)(cyclohexyl)) | 1160 | 7 |
| XIII (Y' = —HN(cyclohexyl)) | 1170 | 5 |

TABLE I-continued

| Stabilizer used | Xenon W'er-O-Meter (hr) | Oven Aging (days) |
|---|---|---|
| Chimassorb 944 | 1350 | 12 |
| PIP-T(5) where PSP = PSP$_3$ of '092 patent | 1360 | 5 |

The most preferred utility for the compounds of this invention is in film, fiber and other shaped articles of the commercially important resins, many of which are pigmented or dyed with conventional relatively light colors, particularly pastel shades. Many of the compounds of this invention do not interfere with the color imparted by the pigment or dye, yet provide the desired stabilization, which is a highly merchantable trait.

We claim:

1. A class of compounds comprising polysubstituted piperzinones distally linked to a triazine nucleus ("PIP-T"), and bis compounds and oligomers of said PIP-T compounds represented by the structural formula $$\left[ \begin{array}{c} X \\ \diagup N \diagdown N \\ -Y \diagdown N \diagup M \end{array} \right]_n \quad (I)$$

wherein, n is an integer in the range from 1 to about 10, said compound having functional end groups selected from H, OH and Cl when n is greater than 1;

X is a substituent having the following formula (II):

(structure II showing piperazinone with substituents $R_1$–$R_5$, $R_8$, $R_9$, $R_{10}$)

wherein, $R_2$, $R_3$, $R_4$ and $R_5$ independently represent $C_1$–$C_{24}$ alkyl and polymethylene having from 4 to about 7 C atoms which are cyclizable forming a spiro cycloalkylene substituent with the C atom of the piperazinone ring, $R_1$ represents hydrogen or oxygen, $C_1$–$C_{24}$ alkyl, $C_1$–$C_{12}$ hydroxyalkyl, benzyl, allyl, and $C_1$–$C_{12}$ haloalkyl;

$R_8$ and $R_9$ independently represent $C_1$–$C_{24}$ alkyl, and polymethylene having from 4 to about 7 C atoms which are cyclizable;

$R_{10}$ represents H, $C_1$–$C_6$ alkyl and phenyl;

Y may be the same as X or M;

M may be Z or Z', wherein

Z represents a radical selected from the group consisting of Cl, OH, $-N\diagup\diagdown N-R_6 \quad -N\diagup\diagdown O \quad -NHR_6 \quad -N\diagdown^{R_6}_{R_7}$ $-NHAr \quad -N\diagdown^{Ar}_{Ar} \quad \text{and} \quad -N\diagup\diagdown$ $R_6$, $R_7$ represent alkyl having from 2 to about 24 carbon atoms; and $C_4$–$C_7$ cycloalkyl;

Ar represents aryl;

Z' represents a radical selected from the group consisting of $-N\diagup\diagdown N- \quad -NH(CH_2)_pNH-$ $-NHCH_2CH_2N\diagup\diagdown N-$ $\begin{array}{c} CH_3 \quad CH_3 \\ | \quad\quad | \\ -NH-CH-CH_2(OCH_2CH)_x-NH- \end{array}$ $-NH(CH_2)_m-N(R_{10})-(CH_2)_m-NH-$ $-HNCH_2CH_2-N(-CH_2CH_2NH-)-\underset{\substack{N\diagup\diagdown N \\ Z\diagdown N \diagup Z}}{}$ $-NH(CH_2)_3N(R_{10})(CH_2)_3NH-$ $-NH-\bigcirc-C(R_{10})(R_{10})-\bigcirc-NH-$ $-N\diagup\diagdown-(CH_2)_p-\diagdown\diagup N-$ $-O-\bigcirc-C(Me)(Me)-\bigcirc-O-$ $-O-\bigcirc(Me,Me)-C(Me)(Me)-\bigcirc(Me,Me)-O-$ Me = methyl -continued

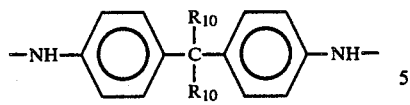

p represents an integer in the range from 2 to about 20;
x represents an integer in the range from 1 to about 50;
m represents an integer in the range from 2 to about 4 and, when n=1, Y and M may be the same as X.

2. The compounds of claim 1 having the structural formula

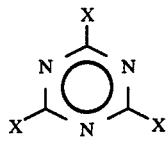 (III)

3. The compounds of claim 1 having the structural formula

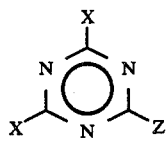 (IV)

4. The compounds of claim 1 having the structural formula

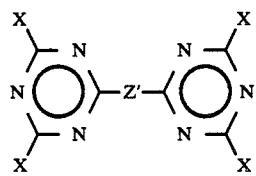 (Va)

and

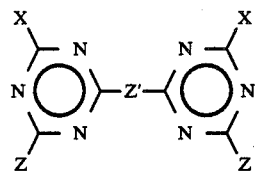 (Vb)

5. The compounds of claim 1 having the structural formula

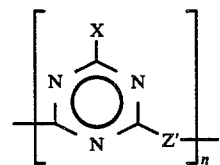 (VI)

6. A class of compounds comprising acyclic polyalkylenepolyamines ("PAPA") having a pendant substituent at each nitrogen atom to form a PAPA with a pendant triazine nucleus at each nitrogen atom to form a pendant piperazinone-triazine ("P[PIP-T]") having the structure

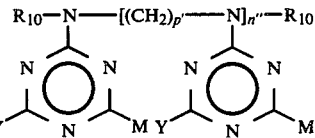

wherein
p' is an integer in the range from 2 to 8;
$R_{10}$ represents H, $C_1$–$C_6$ alkyl and phenyl;
n" is an integer in the range from 2 to 12;
Y and M may be the same or different and is selected from the group consisting of PSP, —NHC$_{12}$H$_{25}$; —N—(C$_2$H$_5$)$_2$; —N—(C$_4$H$_9$)$_2$; —N—(C$_3$H$_7$)$_2$;

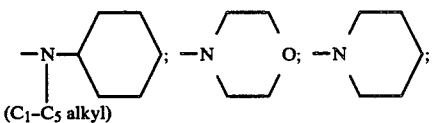

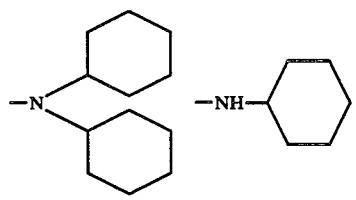

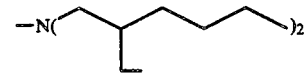 and

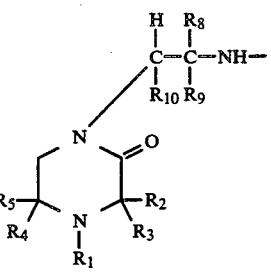

PSP is a substituent having the formula wherein,
$R_2$, $R_3$, $R_4$ and $R_5$ independently represent $C_1$–$C_{24}$ alkyl and polymethylene having from 4 to about 7 C atoms which are cyclizable forming a spiro cycloalkylene substituent with the C atom of the piperazinone ring,
$R_1$ represents hydrogen of oxygen, $C_1$–$C_{24}$ alkyl, $C_1$–$C_{12}$ hydroxyalkyl, benzyl, allyl, and $C_1$–$C_{12}$ haloalkyl;
$R_8$ and $R_9$ independently represent $C_1$–$C_{24}$ alkyl, and polymethylene having from 4 to about 7 C atoms which are cyclizable;
Y may be the same as M;
M may be Z or Z', wherein
Z represents a radical selected from the group consisting of Cl, OH,

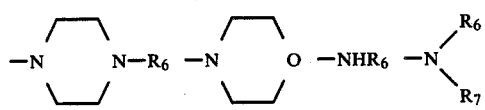

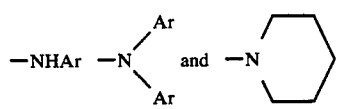

R6, R7 represent alkyl having from 2 to about 24 carbon atoms; and C4–C7 cycloalkyl;
Ar represents aryl;
Z' represents a radical selected from the group consisting of

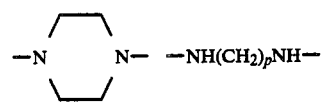

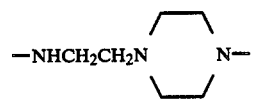

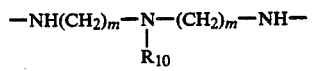

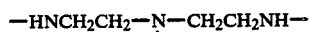

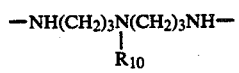

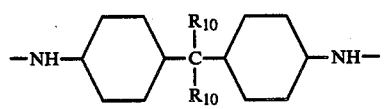

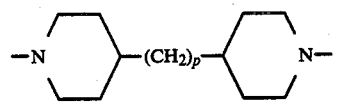

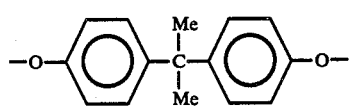

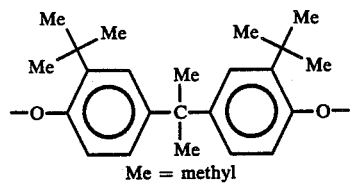

Me = methyl

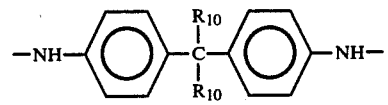

p represents an integer in the range from 2 to about 20;
x represents an integer in the range from 1 to about 50;
m represents an integer in the range from 2 to about 4 and,
Y and M may be the same.

7. The compounds of claim 1 wherein
X is a residue of a polysubstituted piperazinone ("PSP") said "PSP" residue having a structure selected from the group consisting of

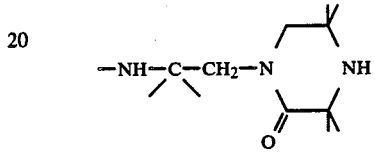

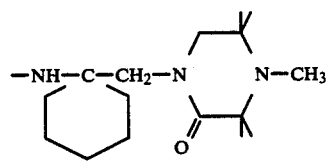

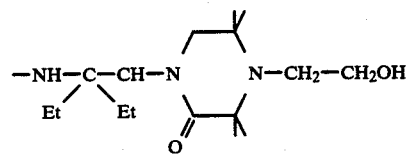

and M and Y are independently selected from the group consisting of

OH, NHC12H25, N(C4H9)2, N—[CH2CH(Et)C4H9]2,

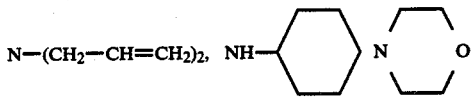

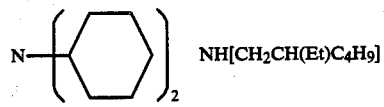

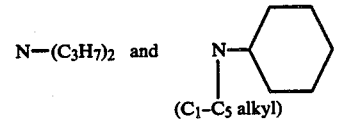

(C1–C5 alkyl)

8. The compounds of claim 7 including:
1,1'-[(6-cyclohexylamino-1,3,5-triazine-2,4-diyl)bis-[imino(2,2-dimethyl-2,1-ethanediyl)]]bis[3,3,5,5-tetramethylpiperazinone];
1,1'-[6-(2-ethylhexyl)amino-1,3,5-triazine-2,4-diyl]bis-[imino(2,2-dimethyl-2,1-ethanediyl)]]bis[3,3,5,5-tetramethylpiperazinone]; and, 1-[2-[[4,6-di(cyclohexylamino)-1,3,5-triazin-2-yl]-amino]-2-methylpropyl]-3,3,5,5-tetramethylpiperazinone.

9. The compounds of claim 4 including: poly[[6-[[1,1-dimethyl-2-(3,3,5,5-tetramethyl-2-oxo-1-piperazinyl)ethyl]amino]-1,3,5-triazine-2,4-diyl-]imino-1,2 ethanediyl-1,4-piperazinediyl].

10. An organic polymeric composition of matter resistant to degradation by ultraviolet light said composition having dispersed therein from about 0.01 parts to about 5 parts by weight of a stabilizer compound consisting of a polysubstituted piperazinone distally linked to a triazine nucleus, per 100 parts of said organic material, said stabilizer compound being represented by the structural formula

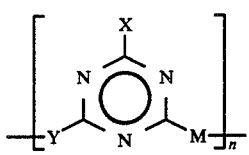

(I)

wherein,
n is an integer in the range from 1 to about 10,
said compound having functional end groups selected from H, OH and Cl when n is greater than 1;
X is a substituent having the following formula (II):

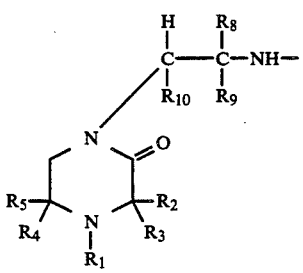

(II)

wherein,
$R_2$, $R_3$, $R_4$ and $R_5$ independently represent $C_1$–$C_{24}$ alkyl and polymethylene having from 4 to about 7 C atoms which are cyclizable forming a spiro cycloalkylene substituent with the C atom of the piperazinone ring,
$R_1$ represents hydrogen or oxygen, $C_1$–$C_{24}$ alkyl, $C_1$–$C_{12}$ hydroxyalkyl, benzyl, allyl, and $C_1$–$C_{12}$ haloalkyl;
$R_8$ and $R_9$ independently represent $C_1$–$C_{24}$ alkyl, and polymethylene having from 4 to about 7 C atoms which are cyclizable;
$R_{10}$ represents H, $C_1$–$C_6$ alkyl and phenyl;
Y may be the same as X or M;
M may be Z or Z', wherein
Z represents a radical selected from the group consisting of Cl, OH,

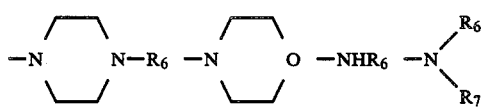

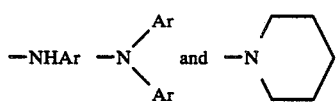

$R_6$, $R_7$ represent alkyl having from 2 to about 24 carbon atoms; and $C_4$–$C_7$ cycloalkyl;
Ar represents aryl;
Z' represents a radical selected from the group consisting of

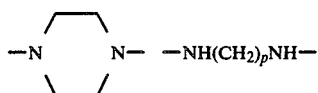

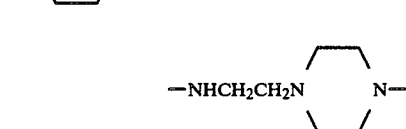

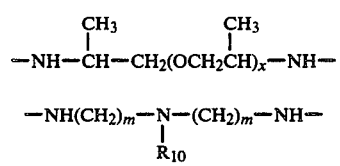

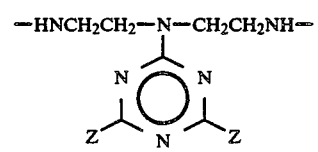

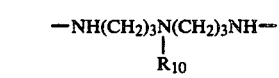

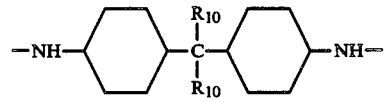

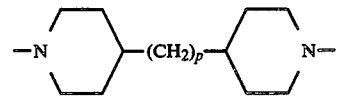

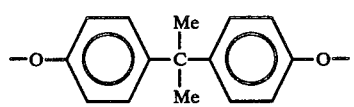

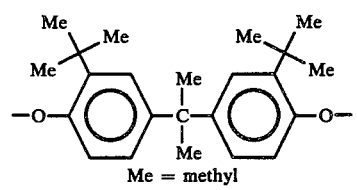

Me = methyl

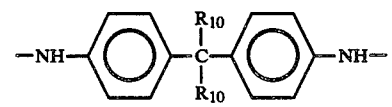

p represents an integer in the range from 2 to about 20;
x represents an integer in the range from 1 to about 50;
m represents an integer in the range from 2 to about 4 and,
when n=1, Y and M may be the same as X.

11. The composition of claim 10 wherein said stabilizer compound has the structural formula

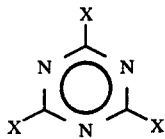

12. The composition of claim 10 wherein said stabilizer compound has the structural formula

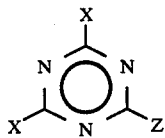

(IV)

13. The composition of claim 10 wherein said stabilizer compound has the structural formula

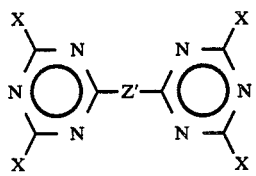

(Va)

and

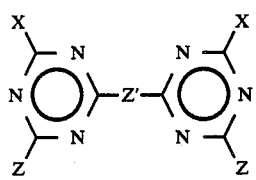

(Vb)

14. The composition of claim 10 wherein said stabilizer compound has the structural formula

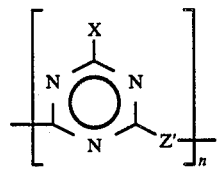

(VI)

15. The composition of claim 10 wherein said X is a residue of a polysubstituted piperazinone ("PSP") said "PSP" residue having a structure selected from the group consisting of

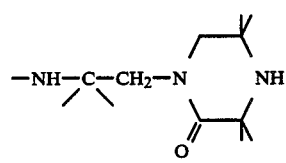

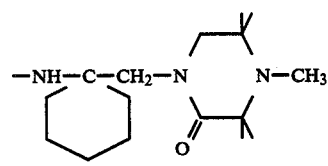

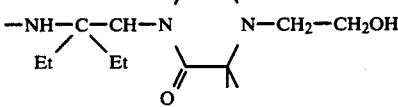

and M and Y are independently selected from the group consisting of

OH, NHC$_{12}$H$_{25}$, N(C$_4$H$_9$)$_2$, N—[CH$_2$CH(Et)C$_4$H$_9$]$_2$,

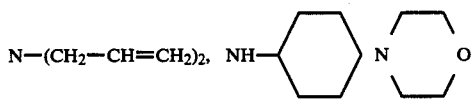

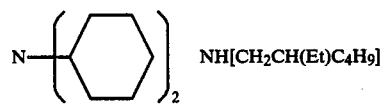

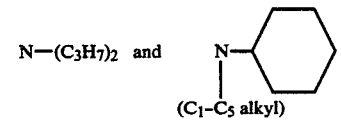

16. The composition of claim 10 wherein said stabilizer compound is selected from the group consisting of
1,1'-[(6-cyclohexylamino-1,3,5-triazine-2,4-diyl)bis-[imino(2,2-dimethyl-2,1-ethanediyl)]]bis[3,3,5,5-tetramethylpiperazinone];
1,1'-[6-(2-ethylhexyl)amino-1,3,5-triazine-2,4-diyl]bis-[imino(2,2-dimethyl-2,1-ethanediyl)]]bis[3,3,5,5-tetramethylpiperazinone];
1-[2-[[4,6-di(cyclohexylamino)-1,3,5-triazin-2-yl]-amino]-2-methylpropyl]-3,3,5,5-tetramethylpiperazinone; and,
poly[[6-[[1,1-dimethyl-2-(3,3,5,5-tetramethyl-2-oxo-1-piperazinyl)ethyl]amino]-1,3,5-triazine-2,4-diyl]-imino-1,2 ethanediyl-1,4-piperazinediyl].

17. A composition of matter resistant to degradation by ultraviolet light comprising an organic material subject to ultraviolet light degradation having dispersed therein from about 0.01 part to about 5 parts by weight of a stabilizer compound consisting of an acyclic polyalkylene polyamine having substituted at the N atoms thereof a polysubstituted piperazinone distally linked to a triazine nucleus, per 100 parts of said organic material, said stabilizer compound being represented by the structural formula

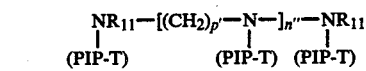

wherein (PIP-T) is represented by the residue of

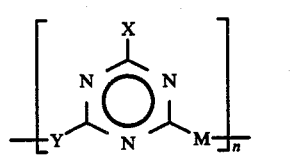

(I)

wherein,
n is an integer in the range from 1 to about 10,
said compound having functional end groups selected from H, OH and Cl when n is greater than 1;
X is a substituent having the following formula (II):

$$\begin{array}{c} H \quad R_8 \\ | \quad | \\ C\text{—}C\text{—}NH\text{—} \\ | \quad | \\ R_{10} \quad R_9 \end{array} \quad \text{(II)}$$

(piperazinone ring with N, O, R_1–R_5 substituents)

wherein,
R$_2$, R$_3$, R$_4$ and R$_5$ independently represent C$_1$–C$_{24}$ alkyl and polymethylene having from 4 to about 7 C atoms which are cyclizable forming a spiro cycloalkylene substituent with the C atom of the piperazinone ring,
R$_1$ represents hydrogen or oxygen, C$_1$–C$_{24}$ alkyl, C$_1$–C$_{12}$ hydroxyalkyl, benzyl, allyl, and C$_1$–C$_{12}$ halcalkyl;
R$_8$ and R$_9$ independently represent C$_1$–C$_{24}$ alkyl, and polymethylene having from 4 to about 7 C atoms which are cyclizable;
R$_{10}$ represents H, C$_1$–C$_6$ alkyl and phenyl;
Y may be the same as X or M;
M may be Z or Z', wherein
Z represents a radical selected from the group consisting of Cl, OH, $$-N\bigcap N-R_6 \quad -N\bigcap O \quad -NHR_6 \quad -N\begin{array}{c} R_6 \\ R_7 \end{array}$$

$$-NHAr \quad -N\begin{array}{c} Ar \\ Ar \end{array} \quad \text{and} \quad -N\bigcap$$

R$_6$, R$_7$ represent alkyl having from 2 to about 24 carbon atoms; and C$_4$–C$_7$ cycloalkyl;
Ar represents aryl;
Z' represents a radical selected from the group consisting of $$-N\bigcap N- \quad -NH(CH_2)_pNH-$$

$$-NHCH_2CH_2N\bigcap N-$$

$$\begin{array}{c} CH_3 \quad\quad CH_3 \\ | \quad\quad\quad | \\ -NH-CH-CH_2(OCH_2CH)_x-NH- \end{array}$$

$$-NH(CH_2)_m-N-(CH_2)_m-NH- \\ \quad\quad\quad | \\ \quad\quad\quad R_{10}$$

-continued $$-HNCH_2CH_2-N-CH_2CH_2NH-$$

(triazine ring with N, Z substituents)

$$-NH(CH_2)_3N(CH_2)_3NH- \\ \quad\quad | \\ \quad\quad R_{10}$$

$$-NH-\bigcirc-\overset{R_{10}}{\underset{R_{10}}{C}}-\bigcirc-NH-$$

$$-N\bigcirc-(CH_2)_p-\bigcirc N-$$

$$-O-\bigcirc-\overset{Me}{\underset{Me}{C}}-\bigcirc-O-$$

$$\begin{array}{c} Me \quad Me \quad\quad Me \quad Me \\ Me \quad\quad\quad\quad\quad\quad Me \\ -O-\bigcirc-\underset{Me}{\overset{Me}{C}}-\bigcirc-O- \end{array}$$

Me = methyl $$-NH-\bigcirc-\overset{R_{10}}{\underset{R_{10}}{C}}-\bigcirc-NH-$$

p represents an integer in the range from 2 to about 20;
x represents an integer in the range from 1 to about 50;
m represents an integer in the range from 2 to about 4 and,
when n=1, Y and M may be the same as X.

18. The composition of claim 17 wherein said residue has the structural formula (triazine ring with N, M, X substituents)

wherein,
X is a residue of a polysubstituted piperazinone ("PSP") said "PSP" residue having a structure selected from the group consisting of $$-NH-C-CH_2-N\bigcap NH$$
$$\quad\quad\quad\quad\quad\quad O$$

-continued

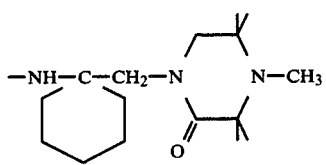

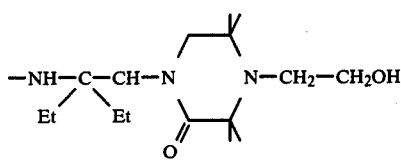

M is selected from the group consisting of

OH, NHC$_{12}$H$_{25}$, N(C$_4$H$_9$)$_2$, N—[CH$_2$CH(Et)C$_4$H$_9$]$_2$,

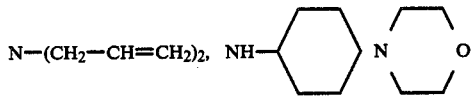

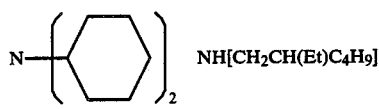

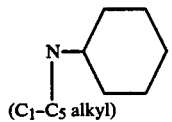

and, M may be the same as X.

19. The composition of claim 18 wherein said stabilizer compound is identified as 1,1'-[[[4-(cyclohexylamino)-6-[[1,1-dimethyl-2-(3-,3,5,5-tetramethyl-2-oxo-1-piperazinyl)ethyl]amino]-1,3,5-triazin-2-yl]imino]bis[2,1-ethanediylimino[6-(cyclohexylamino)-1,3,5-triazine-4,2-diyl]imino(2,2-dimethyl-2,1-ethanediyl]]bis[3,3,5,5-tetramethylpiperazinone].

20. A process for preparing a branched bridge polysubstituted piperazinone ("PSP") having the structure

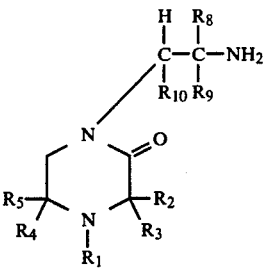

wherein,

R$_2$, R$_3$, R$_4$ and R$_5$ independently represent C$_1$–C$_{24}$ alkyl and polymethylene having from 4 to about 7 C atoms which are cyclizable forming a spiro cycloalkylene substituent with the C atom of the piperazinone ring, R$_1$ represents hydrogen or oxygen, C$_1$–C$_{24}$ alkyl, C$_1$–C$_{12}$ hydroxyalkyl, benzyl, allyl, and C$_1$–C$_{12}$ haloalkyl;

R$_8$ and R$_9$ independently represent C$_1$–C$_{24}$ alkyl, and polymethylene having from 4 to about 7 C atoms which are cyclizable;

R$_{10}$ represents H, C$_1$–C$_6$ alkyl and phenyl; comprising, contacting a polyalkyleneamine having terminal free primary amine groups, represented by the structure

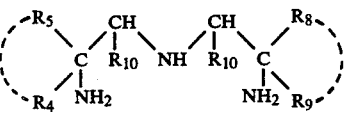

wherein, R$_4$, R$_5$, R$_8$, R$_9$ and R$_{10}$ have the same connotation as that set forth above;

with sufficient amounts of chloroform and a ketone, optionally in the presence of a phase transfer catalyst, at a temperature in the range from about −10° C. to about 30° C., to yield said PSP.

* * * * *

UNITED STATES PATENT AND TRADEMARK OFFICE
CERTIFICATE OF CORRECTION

PATENT NO. : 4,629,752
DATED : December 16, 1986
INVENTOR(S) : Robert W. Layer, John T. Lai, and Pyong N. Son It is certified that error appears in the above—identified patent and that said Letters Patent is hereby corrected as shown below:

Column 20, Line 61, "$-NHC_{12}H_{25}; -N-(C_2H_5)_2; -N-(C_4H_9)_2; -N-(C_3H_7)_2;$" should read:

$-N-(C_4H_9)_2; -N-(C_3H_7)_2;$

Column 37, Line 12, "$-NH-C-CH-N\begin{matrix}/ \\ \backslash\end{matrix}\begin{matrix}\backslash \\ /\end{matrix}N-CH_2-CH_2OH$"

should read: $-NH-C-CH-N\begin{matrix}/ \\ \backslash\end{matrix}\begin{matrix}\backslash \\ /\end{matrix}N-CH_2OH$ Signed and Sealed this Twelfth Day of April, 1988

Attest:

DONALD J. QUIGG

Attesting Officer   Commissioner of Patents and Trademarks